United States Patent [19]
Viccaro

[11] 4,430,324
[45] Feb. 7, 1984

[54] AMMONIUM FLUOROMETALLATE CONTAINING COMPOSITIONS

[75] Inventor: John P. Viccaro, Whitestone, N.Y.

[73] Assignee: Lever Brothers Company, New York, N.Y.

[21] Appl. No.: 415,111

[22] Filed: Sep. 7, 1982

Related U.S. Application Data

[63] Continuation of Ser. No. 325,458, Nov. 27, 1981, abandoned.

[51] Int. Cl.$^3$ .......................... A61K 7/18; A61K 7/22; A61K 33/16; A61K 33/30
[52] U.S. Cl. ....................................... 424/52; 424/131; 424/140; 424/144; 424/145; 424/147; 424/151
[58] Field of Search ................. 424/52, 151, 131, 140, 424/144, 147, 145

[56] References Cited

U.S. PATENT DOCUMENTS 3,201,316  8/1965  Norris .................................. 167/93
3,490,866  1/1970  Muhler ................................. 23/88
3,937,804  2/1976  Delaney et al. ....................... 424/52

FOREIGN PATENT DOCUMENTS 8035015  11/1980  Japan .
1188914   4/1970  United Kingdom .
1288892   9/1972  United Kingdom .
2077281  12/1981  United Kingdom .

OTHER PUBLICATIONS

Caries Research 3:315–325, "A Clinical Trial On the Caries-Inhibiting Effect of Sodium Hexafluorostannate" (Moller et al.).
Caries Research 4:269–282, "The Caries Inhibiting Effect of Topically Applied Hexafluorostannate on Dentine and Enamel" (von der Fehr).
Arch. Oral Biol. 1974, 947–950, "Incorporation of Fluoride In Bones and Teeth and Dental Fluorosis in Mice After Administration of Complex Fluorides" (Ruzicka et al.).
J. Am. Dent. Assoc. 1978, 96, 459–463, "Dental Fluorosis as Related to the Concentration of Fluoride in Teeth and Bone" (Brudevold et al.).

*Primary Examiner*—Shep K. Rose
*Attorney, Agent, or Firm*—Milton L. Honig; James J. Farrell

[57] ABSTRACT

The present invention discloses a composition, comprising: (i) an amount of ammonium fluorometallate effective to treat, control or substantially prevent oral problems, diseases or conditions; and (ii) a carrier for said fluorometallate suitable for use in the oral cavity. It also discloses a method for treating, controlling or substantially preventing oral problems, diseases or conditions which consists essentially of contacting dental tissues, surfaces or oral cavity with ammonium fluorometallate or a preparation thereof including nonfluoro ammonium metallate.

22 Claims, No Drawings

AMMONIUM FLUOROMETALLATE CONTAINING COMPOSITIONS

This is a continuation application of Ser. No. 325,458 filed Nov. 27, 1981, now abandoned.

This invention relates to compositions containing ammonium fluorometallates and methods of using the same.

The efficacy of fluorine in the prevention of dental caries is well established (see for example U.S. Pat. Nos. 3,029,191, 3,070,510 and 3,227,617). The acceptance of fluoride ions as an anticariogenic agent is based essentially on the observation that among the many topical agents that have been tested in clinical trials only those that contain fluorine have been effective in reducing caries. Fluorine-free salts tested have not prevented caries formation. Although fluorides are effective anticaries agents, the mechanism whereby fluorine protects teeth from caries is still not fully understood. There appears to be sufficient evidence, however, to support the following hypotheses. The fluoride ion converts to a small extent the primary material in tooth enamel, hydroxyapatite, to fluoroapatite. This reaction product formed on or near the tooth surface is less susceptible to acid attack than the unmodified hydroxyapatite. The solubility of fluoroapatite in lactic acid is about one-one hundredth of hydroxyapatite. Fluorine also facilitates the remineralization of enamel with hydroxyapatite causing the hydroxyapatite to precipitate at lower concentrations of calcium and phosphate ions. In addition, fluoride ions interfere with the growth and metabolism of acid forming bacteria in plaque, thereby reducing the conversion of sugars to organic acids. These end products of fermentation, primarily lactic acid, promote caries by demineralizing the tooth enamel.

Whether the above mechanisms and others that may be proposed are valid in part or in whole, is not yet determined; however, the general consensus among dental researchers is that one of the strategies to follow in caries reduction is to increase the resistance of teeth to decay via the use of fluoride salts and to find ways to combat the cariogenic bacteria.

Various fluoride salts have been employed as anticariogenic agents. However, the utility of anticariogenic agents has been limited by the extent of their solubility in an aqueous medium, e.g., strontium fluoride.

Stability of a compound in aqueous solutions is another factor to be considered in the use of anticariogenic agents. For example, stannous ions are subject to oxidation and hydrolysis and, for that reason stannous containing compositions must ordinarily be in freshly prepared form or must be used in conjunction with complexing anions in order to obtain its optimal anticariogenic effect (see, for example, U.S. Pat. No. 3,678,153 for a discussion of this aspect).

Hydrogen or hydroxyl ion concentration (pH) of a composition is also an important factor in the efficacy of anticariogenic agents. For instance, the incorporation of water-soluble stannous compounds in dentrifice compositions has presented a problem, since the stannous ions which are formed in the toothpaste tend to react with other components of the toothpaste to form insoluble compounds such as stannous hydroxide or stannous orthophosphate, or to form complexes with other components of the toothpaste. This is particularly true when the pH of the toothpaste is greater than about 6.0.

Taste, effect on the coloration of the teeth, and antibacterial activity of the compound or composition are some of the other factors in addition to those discussed above in the formulation and development of oral preparations.

A liquid or a stable aqueous solution of silver ammonia fluoride for the prevention and treatment of dental diseases has been proposed (see U.S. Pat. No. 3,567,823). The preparation of such compounds requires the use of rather expensive silver compounds which are not usually available in highly purified form and it also requires the introduction of gaseous ammonia to obtain a freshly prepared solution, the freshly prepared solution being preferred. It has been discovered that the instant invention obviates such problems and provides solid ammonium fluorometallates which are stable and have many advantages which will become apparent to those conversant with the art. It is, therefore, an object of the present invention to minimize the disadvantages and limitations of the prior art.

Another object of this invention is to determine which cations are most toxic to cariogenic bacteria and in turn combine this characteristic with the anticariogenic attributes of fluorine.

It is a further object of this invention to provide stable, more soluble ammonium fluorometallate complex having substantially 100% fluoride ion availability and having relatively low toxicity to mammals.

It is yet another object of the present invention to provide anticariogenic ammonium fluorometallates having low metallic-astringent taste and being usable in the preparation of oral compositions.

Other objects and advantages will appear as the description proceeds.

The attainment of the above objects is made possible by this invention which includes methods and compositions which comprise as an active ingredient an effective amount of an ammonium fluorometallate for the control, treatment or prevention of oral problems, diseases or conditions. The ammonium fluorometallates may be used alone or in combination or admixture with other components or ingredients including prophhylactic agents or pharmacological media or vehicles.

Ammonium fluorometallates, particularly $Sn(NH_4)_2F_6$, $ZnNH_4F_3$ and $CoNH_4F_3$ were synthesized according to the method of Haendler and Johnson (J. Am. Chem. Soc. 80: 2662, 1958). $ZnNH_4Cl_3$ and $CoNH_4Cl_3$ were prepared according to the methods described in "A Comprehensive Treatise on Inorganic & Theoretical Chemistry", J. W. Mellor, Vol. IV, p. 551 and Vol. XIV, p. 637, Longmans, Green & Co., London, $AlNH_4(SO_4)_2$ and $CoF_2$, reagent grade, were purchased from Pfaltz-Bauer, Stamford, CT. Other inorganic salts, e.g. $Al_2(SO_4)_3$, $CaCl_2$, $CoCl_2$, $FeNH_4$ citrate, $MgSO_4$, $MnSO_4$, $SnCl_2$, NaCl, KCl, $ZnSO_4$, $Zr(SO_4)_2$, NaF, $SnF_2$, C.P. grade, were purchased from J. T. Baker Chem. Co:, Phillipsburg, NJ, Fisher Scientific Co., Fairlawn, NJ or Mallinckrodt Chem. Works, St. Louis. MO.

Cariogenic Bacteria used for testing the effect of ammonium fluorometallates were *Streptoccus mutans* 6715 and *Streptococcus sanguis* 10556 and 10557, obtained from (ATCC), American Type Culture Collection; Rockville, MD. *Streptococcus salivarius* strains SS4 and H257, and *Streptococcus mutans* OMZ-176 were obtained from Islewo th Lab., Unilever Ltd., Isleworth, England. *Lactobacillus casei*, a human isolate, was obtained from an in-house panelist. All of the above organisms were maintained as lyophilized cultures until the time for use.

The elemental analyses of $ZnNH_4F_3$, $Sn(NH_4)_2F_6$ and $CoNH_4F_3$, which are solid at normal temperature and pressure, were performed by Schwarzkopf Microanalytical Laboratory, Woodside, NY, and were as follows.

| Formula | Theoretical % | | Analytical % | |
|---|---|---|---|---|
| $ZnNH_4F_3$ | Zn | 46.58 | Zn | 46.90 |
| | $NH_4$ | 12.83 | $NH_4$ | 12.26 |
| | F | 40.59 | F | 40.96 |
| $Sn(NH_4)_2F_6$ | Sn | 44.18 | Sn | 45.64 |
| | $NH_4$ | 13.41 | $NH_4$ | 12.65 |
| | F | 42.41 | F | 43.14 |
| $CoNH_4F_3$ | Co | 44.18 | Co | 43.58 |
| | $NH_4$ | 13.45 | $NH_4$ | 13.90 |
| | F | 42.54 | F | 42.23 |

Some of the other properties of the fluorometallates are listed below.

The $ZnNH_4F_3$ and $Sn(NH_4)_2F_6$ compounds displayed pH values in solution of about 5.8 and 3.8, respectively, as compared to a pH of 3.0 for $SnF_2$. This higher pH characteristic eliminates some of the formulation problems encountered with the strong acid effect from $SnF_2$. The preferred pH of compositions employing these fluorometallates should range from about 3.5 to about 8.0.

1000 ppm $F^-$ solutions of Zn and Co ammonium forms were stable. They did not become hazy on standing after several weeks. On the contrary, a $SnF_2$ solution developed turbidity, probably due to oxy-fluoride formation, after 24 hours at room temperature.

At normal temperature and pressure, Co and Zn ammonium fluorometallates are more soluble ($\approx 2.7\%$) than the corresponding $CoF_2$ and $ZnF_2$ with respective solubilities of 1.5% and 1.6%.

It is well known that $SnF_2$ stains teeth, yellow to brown, after continuous use due to formation of the stannous oxides. No coloration is anticipated with $ZnNH_4F_3$ since the decomposition products, if formed, are white.

Solutions of Co and Zn ammonium fluorides exhibited 100% availability of $F^-$ ion at 1000 and 2500 ppm F levels, while similar concentrations of $SnF_2$ released only 80% and 45%, respectively, of the available F. The stannic ammonium fluoride displayed the same fluoride ionization values as $SnF_2$. The ionized fluoride was determined with the Orion-Selective Fluoride electrode (Model 96-09, Orion Research Inc., Cambridge, Mass.).

All of the ammonium forms (Co, Zn, Sn) were much less astringent and metallic tasting than the corresponding uncomplexed fluoride salts at equal molar concentrations. Furthermore, $ZnNH_4F_3$ was considerably less astringent than the following (ranked in descending order of astringency): zinc phenolsulfonate, $ZnSO_4$ and $ZnF_2$ at 0.11 mM concentrations which would be equivalent to approximately 5000 ppm $F^-$ levels. These results were the unanimous decisions of a blind study consisting of a tasting-panel of three judges.

The Co and Zn ammonium fluorometallates at 1000 ppm F levels had no effect on the transparency or taste of oral compositions.

It is generally agreed that oral bacteria are responsible for tooth decay. Therefore, a reduction of the cariogenic flora usually results in a decrease in caries formation. The inorganic salts used in the present investigation were selected because of their relatively low toxicity to mammals. The inhibitory action of the test compounds was determined by adding each salt, at known concentrations, to a culture of cariogenic bacteria. After 24 hours at 37° C. bacterial growth was monitored as a change in optical density. A dose response curve (concentration of salt vs. growth) for each compound against each bacterial isolate was plotted in order to obtain the concentration of test agent which would cause a 50% inhibition in growth (ID/50). This is a useful ranking index since it is not always possible to obtain complete inhibition with weak germicidal agents. Only those compounds which were able to elicit an ID/50 response were considered as inhibitory agents.

The medium used for bacterial growth experiments was Trypticase Soy Broth (B.B.L.: Baltimore Biological Labs., Baltimore, MD) supplemented with 0.1% Tween 80 (Difco Labs., Detroit, MICH.) and 0.05% sodium thioglycollate (J. T. Baker). The test organisms, as lyophilized cells, were grown overnight in 50 mls of growth medium in a vacuum desiccator with an atmosphere of 97% $CO_2$/3% $H_2$ at 35° C. These cultures were then used at a 0.2% inoculum to prepare second stage seed flasks. The test media (10 ml) consisting of growth medium plus the potential inhibitors, contained in 16×120 mm screw top test tubes, were inoculated with the second stage seed cultures to give an absorbancy reading of 0.05. Immediately after inoculation the cultures were incubated for 24 hours under anaerobic conditions.

The growth medium was sterilized by autoclaving, whereas the potential inhibitors (as aqueous solutions) were sterilized by filtering each solution separately through a Millipore membrane (0.22$\mu$).

Absorbance at 600 nm versus a medium control was used as a measure of growth on a Beckman Model B spectrophotometer. All absorbancy readings were determined in 16 mm×120 mm Kimax test tubes. This instrument was linear to 0.60 OD units; thus, all cultures displaying values above this range were diluted with the control, accordingly.

The results indicate that Ca, Fe, Mg, Mn, Na and K ions had little or no effect on all the bacterial isolates tested whereas Al, Co, Sn, Zn and their ammoniated forms appeared to be the most active cations (Table I). These cations were also generally superior in activity to NaF.

TABLE I

| | INHIBITION OF BACTERIAL GROWTH BY NON-FLUORINE SALT | | | | | | |
|---|---|---|---|---|---|---|---|
| | ID/50 (mM/L) | | | | | | |
| | S. mutans | | S. salivarius | | S. sanguis | | |
| Salts | 6715 | OMZ-176 | SS4 | H-257 | 10556 | 10557 | L. casei |
| $AlNH_4(SO_4)_2$ | 4.25 | 5.72 | 8.40 | 6.40 | 6.25 | 7.30 | 4.49 |
| $Al_2(SO_4)_3$ | 3.56 | 5.91 | 7.80 | 5.40 | 5.55 | 8.45 | 6.45 |
| $CoCl_2$ | 7.72 | 10.60 | 5.96 | 0.55 | 2.89 | 3.84 | >12.0 |
| $CoNH_4Cl_3^{(a)}$ | 9.85 | | 6.75 | | 2.46 | | >12.0 |
| $SnCl_2$ | 2.26 | 3.68 | 1.45 | 3.64 | 1.27 | 1.88 | 3–6.0 |

TABLE I-continued

INHIBITION OF BACTERIAL GROWTH BY NON-FLUORINE SALT

| | ID/50 (mM/L) | | | | | | |
|---|---|---|---|---|---|---|---|
| | S. mutans | | S. salivarius | | S. sanguis | | |
| Salts | 6715 | OMZ-176 | SS4 | H-257 | 10556 | 10557 | L. casei |
| ZnSO$_4$ | 5.74 | 7.50 | 6.00 | 0.75 | 0.36 | 0.40 | 10.45 |
| ZnNH$_4$Cl$_3$[a] | 4.10 | | 6.50 | | 0.46 | | 10.00 |
| Zr(SO$_4$)$_2$ | 10.3 | 10.90 | 9.82 | 7.54 | 4.83 | 8.70 | 6.70 |
| NaF | 7.3 | 16.30 | 13.40 | 3.77 | 1.18 | 1.82 | >12.0 |

The above values are the means of triplicate experiments.
[a]Due to a limited amount of material, half the organisms were excluded from evaluation.

In addition, the inhibitory cations exhibited different specificities. The S. mutans species were more sensitive to Sn ions, while both S. sanguis species and S. salivarius H-257 appeared to be inhibited primarily by Zn and Co ions and their ammoniated complexes. L. casei was by far the most resistant isolate tested; only the stannous salt displayed appreciable effects on this organism. Sn, Co and Zn being the most toxic cations, they were compared as fluoride salts as shown in Table II.

TABLE II

INHIBITION OF BACTERIAL GROWTH BY FLUORIDE SALTS

| | ID/50 (mM/L) | | | | | | |
|---|---|---|---|---|---|---|---|
| | S. mutans | | S. salivarius | | S. sanguis | | |
| Fluoride salts | 6715 | OMZ-176 | SS4 | H-257 | 10556 | 10557 | L. casei |
| NaF | 7.30 | 16.30 | 13.40 | 3.77 | 1.18 | 1.82 | >12.0 |
| CoNH$_4$F$_3$ | 1.70 | 3.20 | 3.10 | 0.40 | 0.26 | 0.61 | >12.0 |
| SnF$_2$ | 1.50 | 2.28 | 2.45 | 0.74 | 0.44 | 0.84 | 2.97 |
| Sn(NH$_4$)F$_6$ | 1.20 | 1.43 | 1.65 | 0.40 | 0.22 | 0.39 | 2.53 |
| ZnNH$_4$F$_3$ | 1.62 | 3.05 | 1.88 | 0.34 | 0.21 | 0.25 | 4.70 |

The above values are the means of triplicate experiments.

It should be noted that all of these compounds inhibited growth and were more inhibitory than the corresponding non-fluoride salts and NaF, with no apparent changes in specificities. These data indicate that the cation portion of the molecule participates in the inhibitory effects exhibited by fluoride salts; that is, the antibacterial activity is not due to the fluoride ion alone. This action becomes more meaningful when the salts were compared on an equal F$^-$ basis since the limiting factor for a fluoride dentifrice will be the F$^-$ concentration set by FDA at the present level of 1000 ppm. The ID/50 values, recalculated as ppm F$^-$, again show (Table III) that all of the fluoride salts containing the aforementioned inhibitory cations were more active than NaF. Also, as previously mentioned, all of the multivalent fluoride salts were quite inhibitory. It should be noted that Sn(NH$_4$)$_2$F$_6$, which is the stannic form of tin, was less active than the stannous form SnF$_2$.

sensitive to Zn and Co ions; whereas S. mutans strains appear to be inhibited primarily by stannous ions. All fluoride salts were toxic to the test organisms and were much more inhibitory than the corresponding nonfluoride salts. The Co and Zn ammoniated forms display similar specificities and activities and are as inhibitory as their non-complexed counterparts, Co and Zn ions. Of particular significance is the fact that the ammoniated cations enhance the antibacterial properties of the fluoride ion. The results further indicate that a mixture of fluoride salts or a combination of a single fluoride salt with one or more of the nonfluoro ammoniated salts (e.g., Cl or SO$_4$) are more efficacious in treating, controlling or substantially preventing oral problems, diseases or conditions than the known dentifrices. These preparations would not only provide the necessary concentrations of fluoride but also display a broader spectrum of activity and greater germicidal properties.

One of the mechanisms whereby fluorine decreases caries formation is that the fluoride reduces the acid solubility of dental enamel. This trait has been demonstrated repeatedly by in vitro dissolution tests. It is well established that the fluoride ion reacts with the hydroxyapatite of tooth enamel to form principally, CaF$_2$ and fluoroapatite. The relative importance of the two products is still questionable but fluoroapatite is more desirable. Nevertheless, in either case the altered tooth's surface is less susceptible to demineralization from acids

TABLE III

INHIBITION OF BACTERIAL GROWTH BY FLUORIDE SALTS

| | ID/50 (ppm F) | | | | | | |
|---|---|---|---|---|---|---|---|
| | S. mutans | | S. salivarius | | S. sanguis | | |
| Salts | 6715 | OMZ-176 | SS4 | H-257 | 10556 | 10557 | L. casei |
| NaF | 138 | 309 | 255 | 72 | 22 | 35 | 352 |
| CoNH$_4$F$_3$ | 97 | 182 | 177 | 23 | 15 | 35 | 684 |
| SnF$_2$ | 56 | 87 | 93 | 29 | 17 | 32 | 113 |
| Sn(NH$_4$)$_2$F$_6$ | 137 | 163 | 188 | 46 | 25 | 45 | 288 |
| ZnNH$_4$F$_3$ | 92 | 174 | 104 | 19 | 12 | 14 | 268 |

The above experiments indicate that each bacterial species is susceptible to varying degrees to different cations. Generally, S. salivarius and S. sanguis are more produced by oral bacteria than the unmodified enamel. The cation of the fluoride salt can also react with dental enamel to yield the corresponding insoluble phosphates which in turn may reduce enamel solubility.

It was, therefore, a purpose of the following study to determine the efficacy of $ZnNH_4F_3$ in reducing hydroxyapatite solubility. The ammoniated salt was compared with $SnF_2$, with NaF and $Na_2FPO_3$ using a dissolution system employing hydroxyapatite discs described by Forward (*Caries Research* 11:9–15, 1977). Demineralization of a hydroxyapatite disc was determined by measuring the amount of phosphate released from a given area (123 mm$^2$) of the disc after a standard exposure time to a buffered solution of the test agent in the following manner. Hydroxyapatite discs of uniform size (13 mm dia.) were prepared by cold vacuum compression of a mixture of column chromatography hydroxyapatite powder (Bio-Gel HTP, Bio-Rad Labs, Richmond, CA) and polyethylene powder. Each disc was embedded in a block of paraffin ($\frac{3}{4}$″ square) exposing only one face. The block was then mounted on a plastic rod which was placed in the chuck of a motor. The mounted discs were hydrated in distilled water for 1 min., avoiding air bubble formation on the disc's surface by slowly rotating the paraffin block. Upon removal, excess water was removed from the disc with a paper tissue. The hydrated discs were subsequently submerged into the buffered test solution for 1 min., followed by a water rinse of 10 ml and a 1 min. immersion in 50 ml of distilled water. The disc was again blotted lightly with a tissue and at this point was ready for dissolution. The block-disc preparation was immersed (depth 3″) in 100 ml of 1 M acetate buffer, pH 4.65 contained in an 8 oz. plastic jar. Dissolution experiments were performed at 37° C. by rotating the mounted discs at 350 rpm±10 rpm for 30 minutes. After this time the extent of reaction of the test compound with the hydroxyapatite disc was determined by analyzing the acetate buffer for phosphate using the method of Chen et al (*Anal. Chem.* 28:1756–1758, 1956). Percent reduction in dissolution was the difference in phosphate levels between a disc treated with buffered-test agents and a control disc treated with buffer alone.

Table IV shows the relative demineralization occurring when hydroxyapatite is exposed to buffered solutions of the representative fluoride. It can be seen that the degree of demineralization caused by 1000 ppm fluoride solutions varies with each fluoride salt and the pH of the solution, but in every case dissolution was reduced, particularly at the lower pH values. This is consistent with past evidence that acidic conditions increase the rate of formation of $CaF_2$ and fluoroapatite. The results also indicate that the Sn and $ZnNH_4$ salts are similar in activity and both are considerably more effective in reducing demineralization than NaF and $Na_2FPO_3$ at all pH values. These data indicate that the presence of $ZnNH_4$ cations enhance the anti-cariogenic effects of fluoride.

TABLE IV

DISSOLUTION OF HYDROXYAPATITE DISCS FOLLOWING FLUORIDE TREATMENT

| Fluoride Solutions at 1000 ppm F$^-$ Conc. | pH | % Reduction in Dissolution |
|---|---|---|
| NaF | 4.0 | 44 |
| NaF | 5.0 | 36 |
| NaF | 6.0 | 31 |
| NaF | 7.0 | 31 |
| $Na_2FPO_3$ | 4.0 | 26 |
| $Na_2FPO_3$ | 5.0 | 23 |
| $Na_2FPO_3$ | 6.0 | 22 |
| $Na_2FPO_3$ | 7.0 | 20 |
| $SnF_2$ | 4.0 | 57 |
| $SnF_2$ | 5.0 | 54 |
| $SnF_2$ | 6.0 | 45 |
| $SnF_2$ | 7.0 | 43 |
| $ZnNH_4F_3$ | 4.0 | 52 |
| $ZnNH_4F_3$ | 5.0 | 49 |
| $ZnNH_4F_3$ | 6.0 | 43 |
| $ZnNH_4F_3$ | 7.0 | 40 |

The above values are the means of triplicate experiments.

Dental plaque is a film on the surface of teeth. This layer is the result of bacterial growth and is composed chiefly of microorganisms, proteinaceous materials and microbial byproducts, such as glucans and organic acids. Plaque is not only primarily responsible for caries formation but it is also implicated in gingival diseases. Because the results described herein above have demonstrated that zinc compounds possess antibacterial activity, it is obvious that $ZnNH_4F_3$ will also reduce plaque formation.

The in vitro test used to compare the antiplaque effects of $ZnNH_4F_3$ vs $ZnSO_4$ is now described.

The in vitro plaque was initiated on uniformly sized aluminum plummets which were previously coated for 20 min. with wax stimulated whole saliva. These coated plummets were then placed in a Trypticase (B.B.L.) 1% sucrose growth medium inoculated with clinical plaque samples. After 5 hours of incubation at 37° C. the plummets were immersed in a solution containing equal volumes of whole saliva and the test compound for one minute and subsequently suspended overnight (37° C.) in a 20% solution of saliva supernatant. On the second day the plummets were retreated with the test solution (1 min.) and reincubated in inoculated Trypticase-sucrose growth medium for 5 hours. After this period of time the plaques were rinsed in distilled water for 5 minutes. The plaques were then removed from the plummets by sonication in 10 ml distilled water and quantitated in a Unicam SP500 spectrophotometer at 570 nm.

A test compound showed antiplaque activity if the plaque mass (O.D. reading) was less than the control plaques treated with water. Five replicas per test compound were examined.

Table V clearly indicates that $ZnNH_4F_3$ is an effective antiplaque agent. $ZnSO_4$ was used as a standard soluble zinc salt and the results obtained are consistent with the bacterial theory of plaque formation.

TABLE V

ANTIPLAQUE STUDY

| Test Solutions Zinc Conc. as mM/L | Percentage Inhibition of Growth of Artificial Plaque* | |
|---|---|---|
| | $ZnSO_4$ | $ZnNH_4F_3$ |
| 6.0 | 47 ± 14 | 45 ± 14 |
| 15.0 | 51 ± 14 | 48 ± 14 |
| 30.0 | 64 ± 14 | 60 ± 14 |

*The values above are means ±95% confidence limits.

The fluoride concentration from $ZnNH_4F_3$ at these test levels does not affect plaque formation (Skjorland, Gjermo & Rolla, *Scand, J. Dent. Res.* 86: 103–117, 1978). There was no difference in activity between $ZnSO_4$ and $ZnNH_4F_3$ and this is consistent with the fact that the zinc is freely available due to the rather weak complexing between the Zn and $NH_4$ (log K 2.18–2.59).

An animal study was conducted to establish the effect of ammoniated fluorides on the incidence of caries. $ZnNH_4F_3$ salt was selected for trial since it displayed in vitro tests those characteristics which are generally associated with caries reduction, such as: lowers the dissolution of hydroxapatite; $F^-$ ions is totally available in solution; inhibits plaque formation; inhibits growth of cariogenic bacteria. In addition, zinc salts are considered less toxic than cobalt salts.

The animal study was conducted as follows. Osborne-Mendel rats were interbred in a closed colony on site and the animals mated randomly. The breeding animals were maintained on a mixed cereal (corn, wheat, soybean) fish and bone meal diet prior to mating. Rats were weaned generally between 22–24 days so that experiments could start at a predetermined date. The animals from one litter were randomly assigned one, or preferably two, to each of the various treatments and the total number of animals per treatment was sixteen. Each animal was weighed, numbered and caged separately in a stainless steel wire cage which restricts cophagy. The animals were then maintained on a cariogenic diet (sugar 66%, skim milk 32%, liver powder 2%) and fed sterile distilled water. The test solution was applied topically with a fine sable haired brush to each rat's molar teeth for 15 sec. twice daily for the first 2 weeks and once daily for the third week. After 21 days the animals were sacrificed with chloroform and weighed. The two separate mandibles and the complete upper jaw were then excised and the mandibles defleshed by means of a scalpel and dental chisel after immersion in neutralized formal saline for 48 hours. The molar teeth were mounted, sectioned longitudinally, and stained with Schiff's reagent and scored by the method of Konig et al, Dtsch. Zahn-, Mund.- and Kieferheilk 29: 99–127 (1958). Using a 40× magnification the lesion in each fissure was rated for its severity on a four point scale, of ATBC. Scoring lesion severity was as follows: (A) Pink coloration in enamel within the fissure; (T) Pink coloration at the enamel-dentine junction but without loss of dentinal material; (B) Coloration and loss of material at the enamel-dentine junction; (C) Loss of enamel material from within the fissure. At the conclusion of the experiment the number of lesions and severity score for each treatment group was averaged and the percent reduction in caries based on the water control was calculated.

The dental caries data are presented in Table VI. Only the severe lesions (B & C) were scored in this experiment since the object of the study was to determine whether a significant difference in performance existed between fluoride compounds. Numerically all of the experimental groups demonstrated a reduction in caries which were statistically significant from the controls; however there was no significant difference in activity between the fluoride salts. While the results achieved with $ZnNH_4F_3$ were not different from the reductions obtained with NaF and NaMFP (sodium monofluorophosphate, $Na_2PO_3F$), they nonetheless demonstrate that significant dental caries reduction can be achieved with $ZnNH_4F_3$ and with other ammoniated fluorides described herein.

TABLE VI
RAT CARIES STUDY

| Group No. | Treatment Solution | $F^-$ ppm | Caries/Rat* | % Reduction |
|---|---|---|---|---|
| 1 | $F^-$ free water | — | 5.25 | — |
| 2 | NaF 0.22% | 1000 | 3.69 | 29.7 |
| 3 | $Na_2PO_3F$ 0.8% | 1000 | 3.69 | 29.7 |
| 4 | $ZnNH_4F_3$ 0.25% | 1000 | 3.63 | 30.9 |

*0.649 - Critical difference in the means at 95% confidence level.

In the preparation of therapeutic or prophylactic compositions incorporating ammonium fluorometallates, a suitable carrier or oral media well known in the art may, of course, be used. Adjuvants such as coloring agents, flavors, humectants, abrasives, detergents, preservatives, emollients and the like and other therapeutic agents compatible with the ammonium fluorometallates may also be included.

The following examples will more fully illustrate the present invention.

EXAMPLE 1

The following stable, non-toxic formulation may be utilized in the preparation of a dentifrice composition incorporating any of the ammonium fluorometallates of this invention. The amount of the ammonium fluorometallates may vary within wide limits governed, among other things, by the toxicity or physiological acceptability of the composition. Since the Food and Drug Administration has presently limited the maximum allowable amount to 1000 ppm of available $F^-$, the example here shows only this level, but lesser or greater amounts can, of course, be used, e.g., about 0.01% to about 3% by weight or from about 50 ppm to about 10,000 ppm, more preferably from about 100 to 3,000 ppm of $F^-$.

| TOOTHPASTE FORMULATION | |
|---|---|
| Abrasive (high density) | 13.00 |
| Abrasive (low density) | 22.00 |
| Sorbitol (70% solution) | 41.50 |
| Ammonium fluorometallate (amount equivalent to 100 ppm $F^-$) | 0.24 |
| Detergent | 7.00 |
| Color | 0.04 |
| Flavor | 3.00 |
| Sodium Saccharin | 0.12 |
| Sodium Benzoate | 0.06 |
| Titanium Dioxide | 0.35 |
| Glycerine | 7.53 |
| Water | Balance to 100% |

EXAMPLE 2

A stable, non-toxic mouthwash composition for the control of cariogenicity or plaque formation according to the teaching of the present invention is prepared as follows. Although the example herein shows 100 ppm of available $F^-$, lesser or greater amounts can, of course, be used, e.g., up to 1000 ppm.

| | |
|---|---|
| Ethanol | 15.00 |
| Propylene Glycol | 10.00 |
| Glycerol | 12.00 |
| Flavor, color | 0.90 |
| Tween 20 | 2.10 |
| Hydrochloric acid (to pH 4.1) | — |
| Detergent | 0.33 |
| Ammonium fluorometallate (amount equivalent to 100 ppm of $F^-$) | 0.024 |
| Buffer | 18.00 |

| -continued | |
|---|---|
| Water | Balance to 100% |

Although the examples herein show the use of ammonium fluorometallates in oral (dentifrice and mouthwash) preparations, the compounds of the present invention may also be incorporated in other preparations or formulations such as chewing gums, lozenges, creams, vitamin formulations, and the like.

It is understood that the examples and embodiments described herein are for illustrative purposes and that various modifications or changes in the light thereof will be suggested to persons skilled in the art and are to be included within the spirit and purview of this application and the scope of the appended claims.

What is claimed is:

1. A composition, comprising:
   (i) an amount of ammonium fluorometallate selected from the group consisting of $ZnNH_4F_3$, $CoNH_4F_3$, $CuNH_4F_3$, $Sn(NH_4)_2F_6$, $MnNH_4F_3$, $FeNH_4F_3$, $Zr(NH_4)_3F_7$, $In(NH_4)_3F_6$ and mixtures thereof, effective to treat, control or substantially prevent plaque formation and dental caries; and
   (ii) a carrier for said fluorometallate suitable for use in the oral cavity.

2. A substantially stable, anticariogenic composition according to claim 1 comprising as an active ingredient an amount of an ammonium fluorometallate in admixture with an acceptable oral medium compatible with said fluorometallate, said amount being effective to control dental caries.

3. A substantially stable, non-toxic composition for controlling plaque according to claim 1 comprising as an active ingredient an amount of an ammonium fluorometallate in admixture with an acceptable oral medium compatible with said fluorometallate, said amount being effective to control said plaque at the site of formation.

4. A composition as defined in claim 1, 2 or 3 wherein the amount of said fluorometallate is about 0.01% to about 3% by weight.

5. A composition as defined in claim 1, 2 or 3 wherein said ammonium fluorometallate is present in an effective amount up to an equivalent of about 1000 ppm of available fluoride ion.

6. A composition according to claim 1 wherein said amount of said Zn or Co ammonium fluorometallates have 100% fluoride ion availability.

7. A composition according to claim 1 wherein said ammonium fluorometallate is mixed with nonfluoro ammonium metallate selected from the group consisting of $ZnNH_4Cl_3$, $CoNH_4Cl_3$, $Sn(NH_4)_2Cl_6$, $Al(NH_4)Cl_4$, $Zn(NH_4)_2(SO_4)_2$, $Co(NH_4)_2(SO_4)_2$, $Sn(NH_4)_2(SO_4)_3$ and $Al(NH_4)(SO_4)_2$.

8. A composition according to claim 1, 2 or 3 wherein said ammonium fluorometallate is a solid at normal temperature and pressure.

9. A composition according to claim 1, 2 or 3 wherein said composition is less astringent and metallic tasting than corresponding uncomplexed fluoride salts at equimolar concentrations such as cobalt fluoride, zinc fluoride or tin fluoride.

10. A composition according to claim 1, 2 or 3 which is in the form of a toothpaste wherein the ammonium fluorometallate is present in an effective amount up to about 1000 ppm of available fluoride ion.

11. A composition according to claim 1, 2 or 3 which is in the form of a mouthwash wherein the ammonium fluorometallate is present in an effective amount up to about 1000 ppm of available fluoride ion.

12. A method for treating, controlling or substantially preventing plaque formation and dental caries which comprises applying to the site thereof a composition containing an amount of an ammonium fluorometallate selected from the group consisting of $ZnNH_4F_3$, $CoNH_4F_3$, $CuNH_4F_3$, $Sn(NH_4)_2F_6$, $MnNH_4F_3$, $FeNH_4F_3$, $Zr(NH_4)_3F_7$, $In(NH_4)_3F_6$ and mixtures thereof, effective to control, treat or substantially prevent said oral problems, diseases or conditions.

13. A method for controlling, treating or substantially preventing dental caries which comprises applying to the site of formation of said dental caries an oral composition containing an effective amount of an ammonium fluorometallate whereby cariogenicity is controlled.

14. A method for controlling plaque formation according to claim 12 comprising applying to the site of said plaque formation a composition comprising an effective amount of an ammonium fluorometallate whereby said plaque formation is controlled.

15. A method according to claim 12, 13 or 14 wherein the amount of said fluorometallate is about 0.01% to about 3% by weight.

16. A method according to claim 12, 13 or 14 wherein said ammonium fluorometallate is present in an effective amount up to about 1000 ppm of available fluoride ion.

17. A method according to claim 12 wherein said amount of said Zn or Co ammonium fluorometallates have 100% fluoride ion availability.

18. A method according to claim 12 wherein said ammonium fluorometallate is mixed with nonfluoro ammonium metallate selected from the group consisting of $ZnNH_4Cl_3$, $CoNH_4Cl_3$, $Sn(NH_4)_2Cl_6$, $Al(NH_4)Cl_4$, $Zn(NH_4)_2(SO_4)_2$, $Co(NH_4)_2(SO_4)_2$, $Sn(NH_4)_2(SO_4)_3$ and $Al(NH_4)(SO_4)_2$.

19. A method according to claim 12, 13 or 14 wherein said ammonium fluorometallate is a solid at normal temperature and pressure.

20. A method according to claim 12, 13 or 14 wherein said composition is less astringent and metallic tasting than corresponding uncomplexed fluoride salts at equimolar concentrations such as cobalt fluoride, zinc fluoride or tin fluoride.

21. A method according to claim 12, 13 or 14 wherein said composition is in the form of a toothpaste wherein the ammonium fluorometallate is present in an effective amount up to about 1000 ppm of available fluoride ion.

22. A method according to claim 12, 13 or 14 wherein said composition is in the form of a mouthwash wherein the ammonium fluorometallate is present in an effective amount up to about 1000 ppm of available fluoride ion.

* * * * *

UNITED STATES PATENT AND TRADEMARK OFFICE
CERTIFICATE OF CORRECTION

PATENT NO. : 4,430,324
DATED : February 7, 1984
INVENTOR(S) : John Peter Viccaro It is certified that error appears in the above—identified patent and that said Letters Patent is hereby corrected as shown below:

Column 12, Claim 13, line 21: after the word "caries"
  it should read -- according to claim 12 --.

Signed and Sealed this

Twenty-eighth Day of May 1985

[SEAL]

Attest:

DONALD J. QUIGG

*Attesting Officer*  *Acting Commissioner of Patents and Trademarks*